United States Patent
Hirano et al.

(10) Patent No.: US 9,144,371 B2
(45) Date of Patent: Sep. 29, 2015

(54) DRAINAGE TUBE INSERTION TOOL

(75) Inventors: Sota Hirano, Kanagawa (JP); Tomohiro Ohki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 180 days.

(21) Appl. No.: 13/434,673

(22) Filed: Mar. 29, 2012

(65) Prior Publication Data
US 2012/0253117 A1    Oct. 4, 2012

(30) Foreign Application Priority Data

Mar. 31, 2011   (JP) ................................. 2011-079220

(51) Int. Cl.
| | | |
|---|---|---|
| *A61B 1/00* | (2006.01) | |
| *A61B 1/04* | (2006.01) | |
| *A61F 2/06* | (2013.01) | |
| *A61B 1/015* | (2006.01) | |

(52) U.S. Cl.
CPC ............. *A61B 1/015* (2013.01); *A61B 1/00073* (2013.01); *A61B 1/00135* (2013.01)

(58) Field of Classification Search
CPC ............... A61B 1/008; A61B 1/00087; A61B 1/00089; A61B 1/00101; A61B 1/00133; A61B 1/00135; A61B 1/0014; A61F 2/958; A61F 2/95; A61F 2/07
USPC ......... 600/104, 106, 107, 114–115, 121–125, 600/156–159; 623/1.11, 1.12
See application file for complete search history.

(56) References Cited

U.S. PATENT DOCUMENTS

| | | | |
|---|---|---|---|
| 6,562,024 B2 * | 5/2003 | Alvarez de Toledo et al. | 604/540 |
| 2002/0188189 A1 * | 12/2002 | Belef et al. | 600/407 |
| 2010/0256729 A1 * | 10/2010 | Mangiardi | 623/1.15 |

FOREIGN PATENT DOCUMENTS

| | | |
|---|---|---|
| JP | 2000-142985 A | 5/2000 |
| JP | 2003-320021 A | 11/2003 |

\* cited by examiner

*Primary Examiner* — Ryan Henderson
(74) *Attorney, Agent, or Firm* — McGinn IP Law Group, PLLC.

(57) ABSTRACT

A drainage tube insertion tool for use in an endoscope, comprising:
  a drainage tube configured to slidably fit on an outer surface of an insertion portion of the endoscope, and
  a pusher tube configured to slidably fit on the outer surface of the insertion portion of the endoscope and which pushes the drainage tube,
  wherein a notch is formed in a side wall portion of the pusher tube along a longitudinal axis direction, and the pusher tube is fitted on the outer surface of the insertion portion upon making a side surface of the insertion portion extend through the notch, and the drainage tube is inserted into a predetermined lumen of a body cavity by pushing the drainage tube out of a distal end of the insertion portion with the pusher tube.

17 Claims, 12 Drawing Sheets

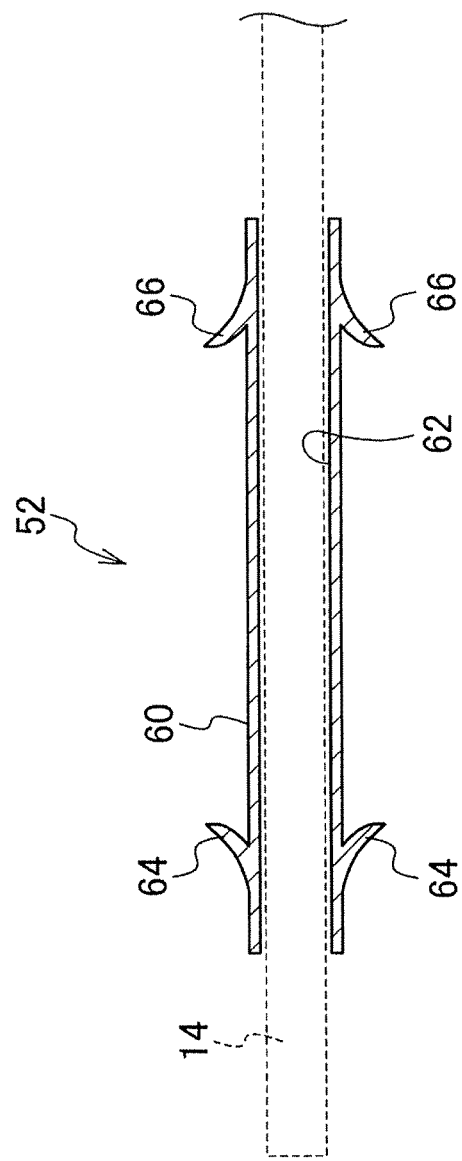

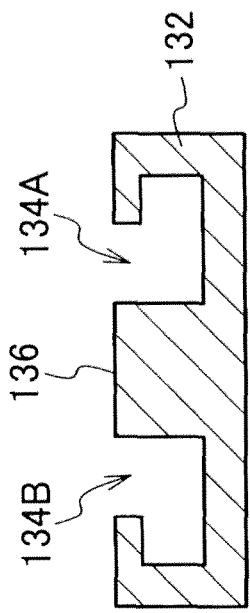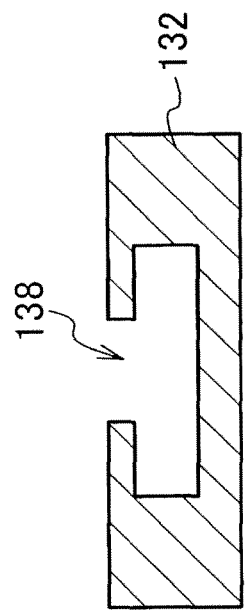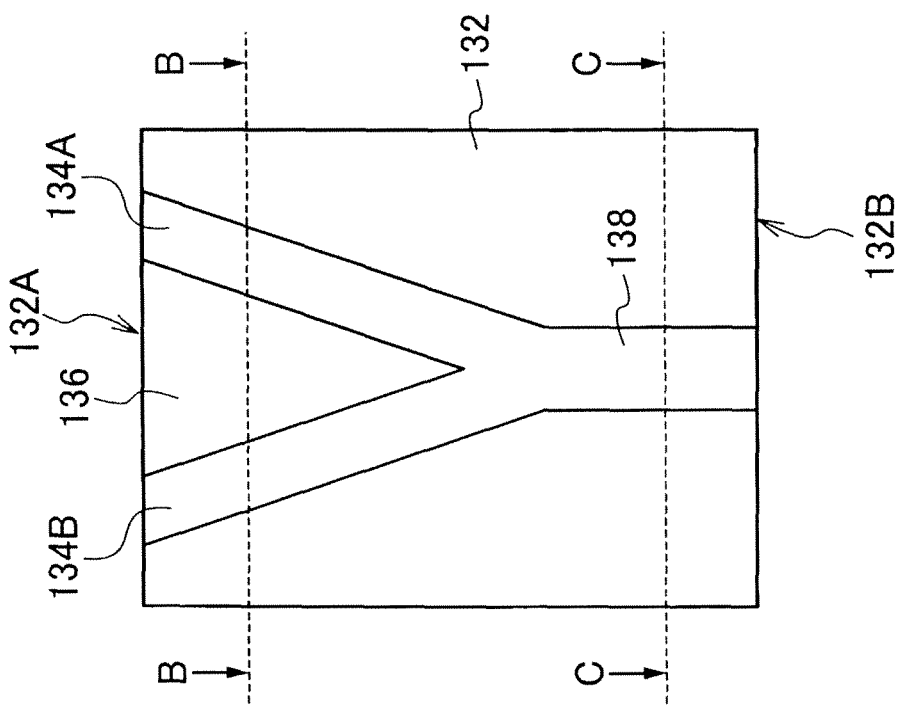

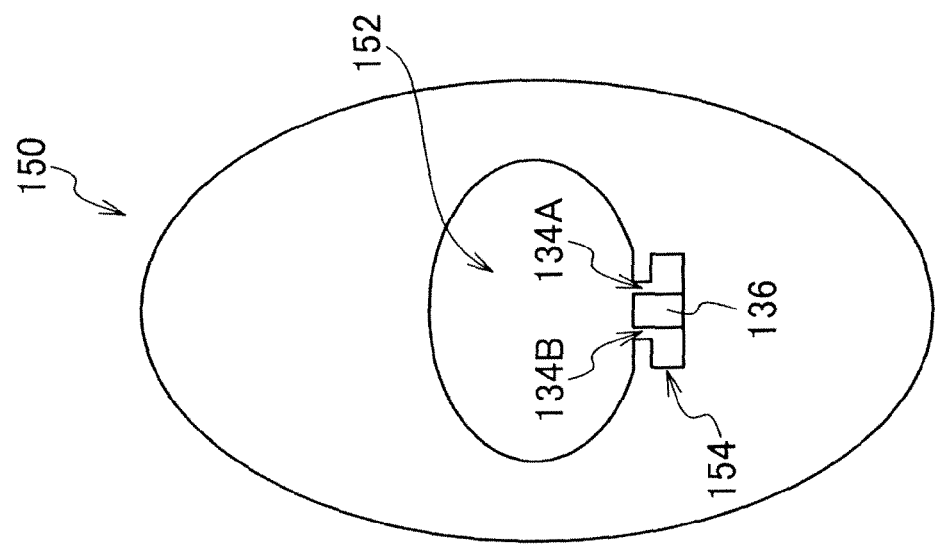
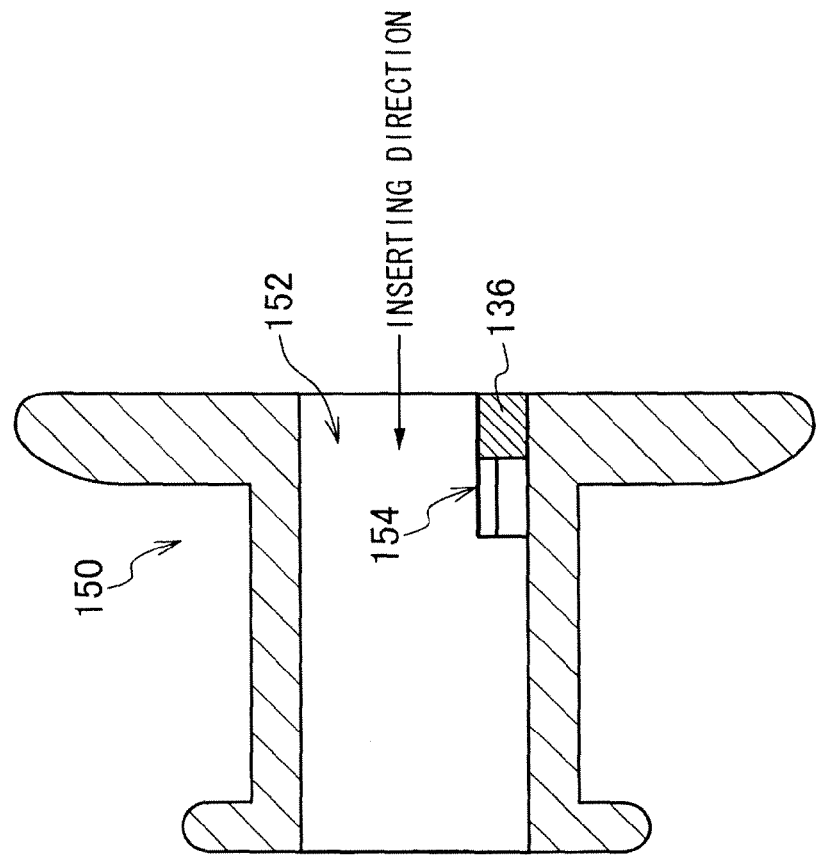

DRAINAGE TUBE INSERTION TOOL

BACKGROUND OF THE INVENTION

1. Field of the Invention

The present invention relates to a drainage tube insertion tool and, more particularly, to a drainage tube insertion tool for inserting and indwelling a drainage tube in the biliary tract or the pancreatic duct.

2. Description of the Related Art

Conventionally, in order to drain bile retained in the biliary tract or pancreatic juice retained in the pancreatic duct into the duodenum, a drainage tube is inserted and indwelled in a constricted region of the biliary tract or pancreatic duct. As a technique of indwelling the drainage tube in the biliary tractor or pancreatic duct, for example, there is available a technique of inserting the insertion portion of a side-viewing endoscope into a portion near the papilla vater of the duodenum, and inserting a guide wire from the papilla vater into the biliary tractor or pancreatic duct through the treatment tool insertion channel of the insertion portion. Then, a guide tube is inserted into the biliary tractor or pancreatic duct by being guided by the guide wire. Thereafter, a drainage tube is fitted on the guide tube and is pushed by pusher tube by being guided by the guide tube, thereby inserting and indwelling the drainage tube in a constricted region in the biliary tractor or pancreatic duct (see, for example, Japanese Patent Application Laid-Open No. 2000-142985 and Japanese Patent Application Laid-Open No. 2003-320021).

SUMMARY OF THE INVENTION

Recently, however, an endoscope has been developed, whose insertion portion has been reduced in diameter so as to be directly inserted into even a small-diameter lumen such as that of the biliary tractor or pancreatic duct. Such endoscope has a treatment tool insertion channel whose inner diameter is small, and hence does not allow to use the conventional technique of inserting the guide tube into the biliary tractor or pancreatic duct through the treatment tool insertion channel. In addition, the insertion portion of the endoscope has been reduced in diameter to an extent to be able to be used as a guide tube which guides the drainage tube.

The present invention has been made in consideration of such a situation, and has as its object to provide a drainage tube insertion tool which allows to insert and indwell a drainage tube in a desired constricted region by using the insertion portion of an endoscope as a guide member without making the drainage tube pass through the treatment tool insertion channel of the insertion portion.

In order to achieve the above object, according to a first aspect of the present invention, there is provided a drainage tube insertion tool for use in an endoscope, comprising: a drainage tube configured to slidably fit on an outer surface of an insertion portion of the endoscope, and a pusher tube configured to slidably fit on the outer surface of the insertion portion of the endoscope and which pushes the drainage tube, wherein a notch is formed in a side wall portion of the pusher tube along a longitudinal axis direction, and the pusher tube is fitted on the outer surface of the insertion portion upon making a side surface of the insertion portion extend through the notch, and the drainage tube is inserted into a predetermined lumen of a body cavity by pushing the drainage tube out of a distal end of the insertion portion with the pusher tube.

According to the present invention, it is possible to insert the drainage tube in a target constricted region by pushing the drainage tube with the pusher tube while using the outer surface of the insertion portion of the endoscope as a guide. In addition, although the pusher tube cannot be fitted on the insertion portion from the proximal end side due to the structure of the endoscope, it is possible to fit the pusher tube on the insertion portion from the side surface owing to the notch formed in the pusher tube without fitting the pusher tube on the insertion portion from the distal end side. This makes it possible to fit the pusher tube on the insertion portion even after the insertion of the insertion portion into the body cavity. That is, the pusher tube does not interfere with the insertion of the insertion portion into a predetermined region in the body cavity.

According to a second aspect of the present invention, in the first aspect, a width of the notch in a direction perpendicular to the longitudinal axis direction is smaller than a diameter of the insertion portion. According to the present invention, this prevents the pusher tube from easily coming off the insertion portion.

According to a third aspect of the present invention, in the first and second aspects, the drainage tube has flexibility.

According to a fourth aspect of the present invention, in the first, second, and third aspects, an operation portion is formed on a proximal end portion of the drainage tube so as to protrude toward the outer surface. According to the present invention, this makes it possible to push the drainage tube while holding the operation portion.

According to a fifth aspect of the present invention, in one of the first to fourth aspects, the notch is helically formed in a predetermined range of the pusher tube in a longitudinal axis direction. According to the present invention, helically forming the notch makes it difficult for the pusher tube to come off the insertion portion, and hence can reliably prevent the pusher tube from coming off the insertion portion due to the bending portion of the insertion portion or the like.

According to a sixth aspect of the present invention, in one of the first to fourth aspects, a fastener is formed in the notch, and the notch is configured to be opened and closed by the fastener. According to the present invention, sealing the notch with the fastener after fitting the pusher tube on the insertion portion of the endoscope makes it difficult for the pusher tube to come off the insertion portion, and hence can reliably prevent the pusher tube from coming off the insertion portion due to the bending portion of the insertion portion or the like.

According to the present invention, it is possible to insert and indwell a drainage tube in a desired constricted region by using the insertion portion of an endoscope as a guide member without making the drainage tube pass through the treatment tool insertion channel of the insertion portion.

BRIEF DESCRIPTION OF THE DRAWINGS

FIG. 3 is a longitudinal sectional view showing an embodiment of a drainage tube;

FIG. 11A is a front view of the slider, FIG. 11B is a sectional view taken along B-B in FIG. 11A, and FIG. 11C is a sectional view taken along C-C in FIG. 11A; and FIG. 12A is a longitudinal sectional view of a mouthpiece, and FIG. 12B is a front view of the mouthpiece.

DETAILED DESCRIPTION OF THE PREFERRED EMBODIMENTS

A preferred embodiment of the present invention will be described in detail below with reference to the accompanying drawings.

Figure 1:
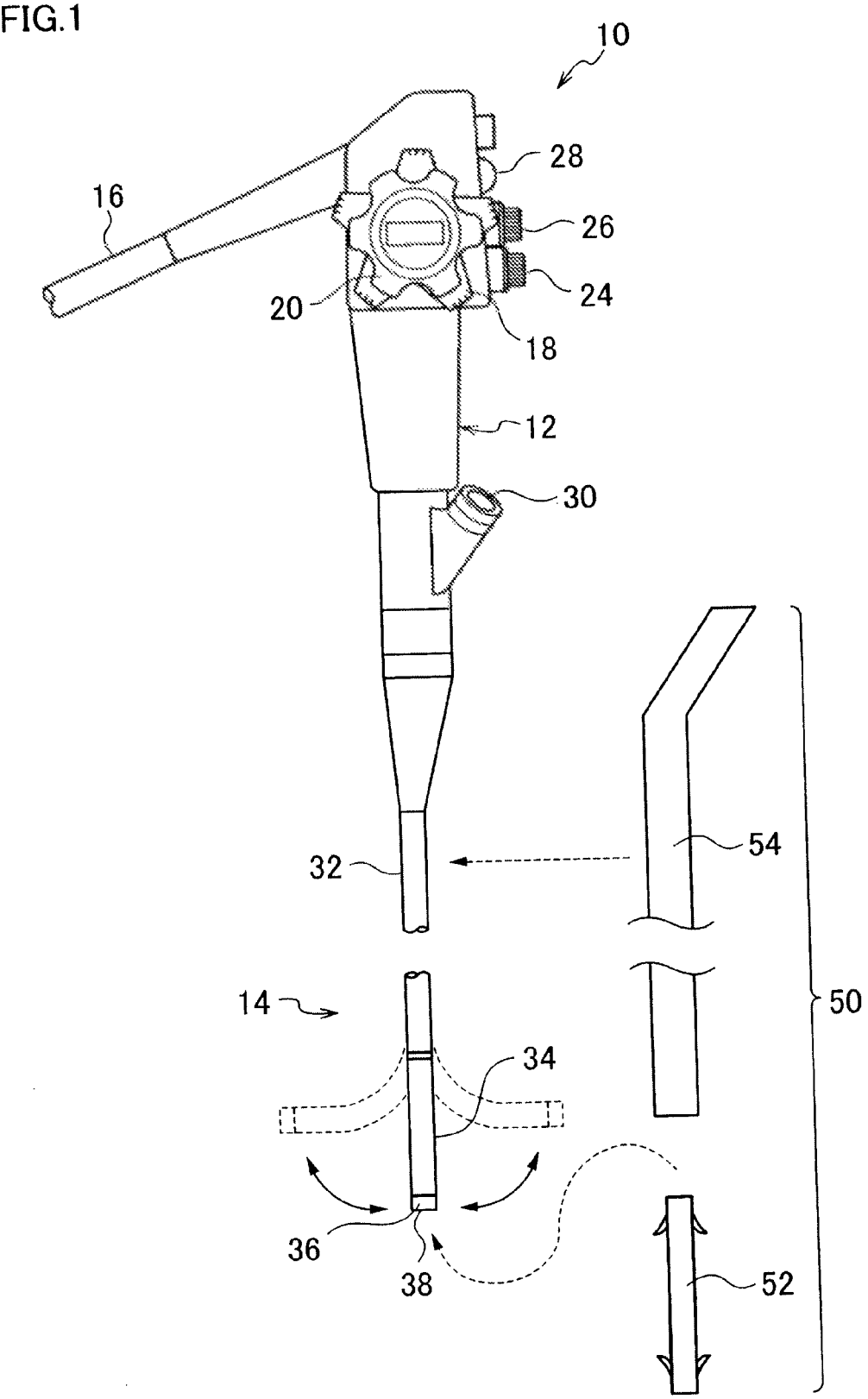
FIG. 1 is an overall view showing an embodiment of an endoscope to which a drainage tube insertion tool according to the present invention and a drainage according to the present invention are applied.

FIG. 1 is an overall view showing an embodiment of an endoscope to which a drainage tube insertion tool according to the present invention and a drainage according to the present invention are applied. An endoscope 10 in FIG. 1 is an endoscope used as a cholangioscope for observing mainly the lumen of the biliary tractor or pancreatic duct (pancreatic-bile system). The endoscope 10 includes an operation portion 12, an insertion portion 14 which is connected in series with the operation portion 12 and inserted into the body cavity, and a universal cable 16 extending from the operation portion 12. At the time of medical treatment, the endoscope 10 is used while being connected to an image processor, light source device, air/water supply device, and suction device (none of which are shown) through the universal cable 16.

The operation portion 12 is a portion which is held by the operator to perform various operations. The operation portion 12 includes various kinds of buttons such as angle knobs 18 and 20 which are rotated, an air/water supply button 24 which is pressed, a suction button 26, and a shutter button 28. The operation portion 12 also includes a treatment tool insertion portion 30 (opening) for the insertion of various kinds of treatment tools into a treatment tool insertion channel extending through the insertion portion 14.

The insertion portion 14 includes, sequentially from the operation portion side, a soft portion 32 having flexibility, a bending portion 34 which bends up and down and left and right in accordance with the operations of the angle knobs 18 and 20, and a hard distal end portion 36.

Figure 2:
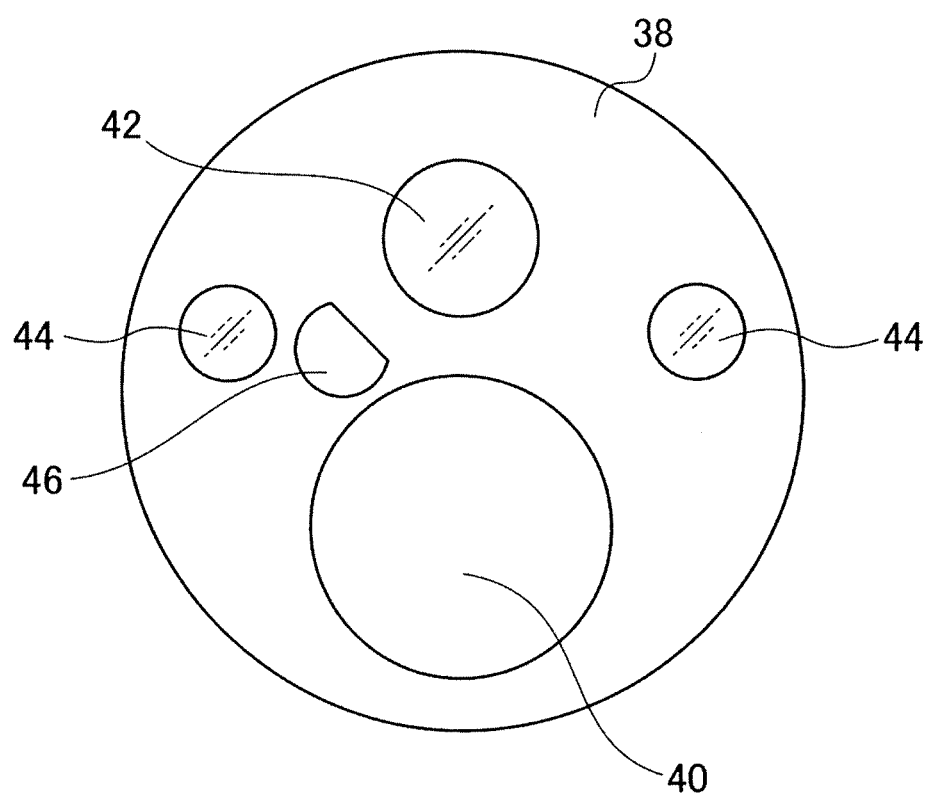
FIG. 2 is a front view showing the distal end face of an insertion portion.

As shown in FIG. 2, a distal end face 38 of the insertion portion 14 is provided with a treatment tool outlet 40, an observation window 42, illumination windows 44, and an air/water supply port 46.

The treatment tool outlet 40 communicates with the treatment tool insertion portion 30 of the operation portion 12 through the treatment tool insertion channel extending through the insertion portion 14. Inserting a treatment tool into the treatment tool insertion portion 30 will make the treatment tool protrude from the treatment tool outlet 40 through the treatment tool insertion channel. The treatment tool insertion channel is also coupled to a suction channel. When the operator presses a suction button 26 of the operation portion 12, blood, mucus, and the like can be sucked from the treatment tool outlet 40 by suction force from the suction device connected to the universal cable 16.

The observation window 42 is disposed on the distal end face 38 as part of the lens of an imaging device (observation device) embedded in the distal end portion 36 or a protective member or the like. The imaging device includes a lens and an imaging element. The lens forms the object light captured through the observation window 42 into an image on the imaging surface of the imaging element. The imaging element then photoelectrically converts the object image formed on the imaging surface to acquire an image signal. The image processor connected to the universal cable 16 receives the image captured by the imaging device as an image signal and performs necessary image processing for the signal. The monitor then displays the resultant image. This allows the operator to observe the image of the interior of the body cavity into which the insertion portion 14 is inserted. When the operator presses the shutter button 28 of the operation portion 12, the image processor records and saves the image captured by the imaging device at this time.

The light exit portion of a light guide is disposed behind the illumination windows 44, from which illumination light is supplied from the light source device, connected to the universal cable 16, through the light guide exits. The illumination light exiting from the illumination windows 44 illuminates an observation target to be imaged by the imaging device.

The air/water supply port 46 communicates with the air/water supply channel extending through the insertion portion 14, and serves to spray, against the observation window 42, the cleaning water and gas supplied from the air/water supply device, connected to the universal cable 16, through the air/water supply channel. The cleaning water and gas sprayed from the air/water supply port 46 clean (and dry) the observation window 42. Blocking the hole formed in the air/water supply button 24 of the operation portion 12 will spray a gas from the air/water supply port 46 toward the observation window 42. Pressing the air/water supply button 24 will spray cleaning water from the air/water supply port 46 toward the observation window 42.

A drainage tube insertion tool 50 according to the present invention includes a drainage tube 52 and a pusher tube 54. The drainage tube 52 is indwelled in a constricted region of the biliary tract or pancreatic duct to secure a channel for bile or pancreatic juice, thereby properly draining bile or pancreatic juice into the duodenum. The pusher tube 54 is used to push the drainage tube 52 into a target constricted region.

Assume that the drainage tube 52 is to be indwelled in a constricted region of the biliary tract or pancreatic duct. In this case, the drainage tube 52 and the pusher tube 54 are fitted on the outer surface of the insertion portion 14. The operator then pushes the drainage tube 52 with the pusher tube 54 by using the insertion portion 14 as a guide member. The operator pushes out the drainage tube 52 from the distal end side of the insertion portion 14, and pushes the drainage tube 52 into a target constricted region, thus indwelling the drainage tube 52 in the constricted region. The drainage tube 52 can be fitted on the outer surface of the insertion portion 14 from the distal end side of the insertion portion 14. The pusher tube 54 can be fitted on the outer surface of the insertion portion 14 by being pushed from the side surface side of the insertion portion 14.

FIG. 3 is a longitudinal sectional view showing a cross-section of the drainage tube 52 taken along the longitudinal axis. As shown in FIG. 3, as is well known, the drainage tube 52 includes a substantially cylindrical tube body 60 having flexibility. The tube body 60 has a lumen 62 penetrating in the longitudinal axis direction. Flap-like stop portions 64 and 66 are formed on the outer surface of the tube body 60 on the distal end side and the proximal end side so as to obliquely protrude toward the middle portion of the tube body 60.

When indwelling the drainage tube 52 in a target constricted region, the operator inserts the insertion portion 14 of the endoscope 10 from the distal end side of the insertion portion 14 into the lumen 62 of the drainage tube 52 to fit the drainage tube 52 on the outer surface of the insertion portion 14. With this operation, the drainage tube 52 is supported on the insertion portion 14 so as to be slidable in the longitudinal axis direction.

Note that the drainage tube 52 is not limited to the arrangement shown in FIG. 3 and may have another known arrangement.

Figure 4A:
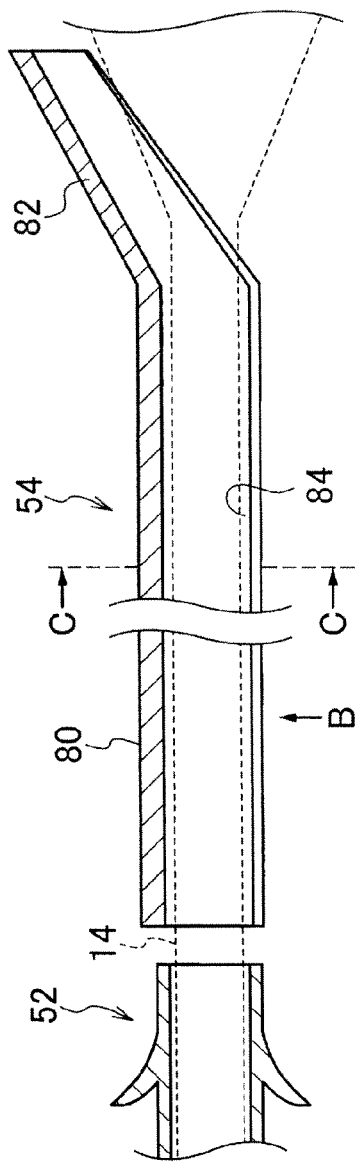
FIGS. 4A to 4C are views showing an embodiment of a pusher tube.
Figure 4B:
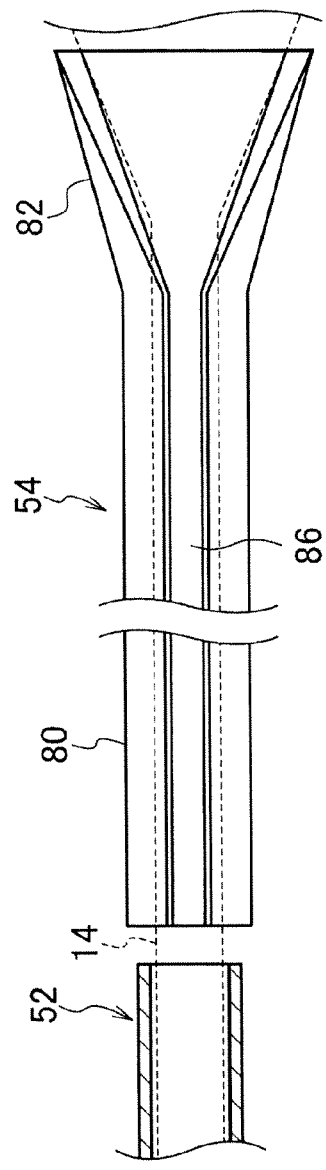
Figure 4C:
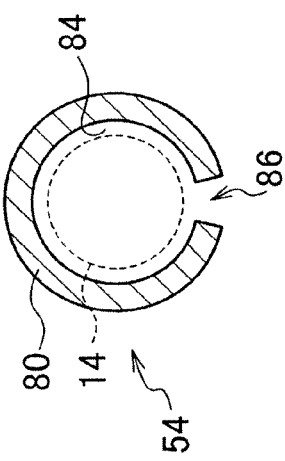

FIGS. 4A to 4C show the arrangement of the pusher tube 54. FIG. 4A is a longitudinal sectional view showing a cross-section of the pusher tube 54 taken along the longitudinal axis. FIG. 4B is a plan view showing the lower surface side of the pusher tube 54 (a plan view when the pusher tube 54 is seen in the direction of an arrow B in FIG. 4A). FIG. 4C is a sectional view (a cross-sectional view) taken along C-C in FIG. 4A.

As shown in FIGS. 4A to 4C, the pusher tube 54 includes a substantially cylindrical tube body 80 having flexibility. The tube body 80 has a lumen 84 penetrating in the longitudinal axis direction. An operation portion 82 extends from the proximal end side of the tube body 80 obliquely upward in the backward direction.

In addition, a notched portion 86 is formed in a lower portion (side wall portion) of the tube body 80 and operation portion 82 so as to extend from the distal end (front end) to the proximal end (rear end). That is, as shown in FIG. 4C, the notched portion 86 is formed so as to make the tube body 80 have a C-shaped cross-section, and the lumen 84 located inside the tube body 80 communicates with the outside. In the operation portion 82, the width of the notched portion 86 (the width of the opening in a direction perpendicular to the longitudinal axis) gradually increases toward the rear end. Note that the width of the notched portion 86 is smaller than the diameter of the insertion portion 14.

When indwelling the drainage tube 52 fitted on the insertion portion 14 in a target constricted region by pushing the insertion portion 14 from the distal end side, the operator fits the pusher tube 54 (tube body 80) on the outer surface of the insertion portion 14 at a position located nearer to the proximal end side than the drainage tube 52. With this operation, the pusher tube 54 is supported so as to be slidable with respect to the insertion portion 14 in the longitudinal axis direction. In this state, the pusher tube 54 can push the drainage tube 52 forward.

When fitting the pusher tube 54 on the outer surface of the insertion portion 14, the operator pushes the pusher tube 54 toward the insertion portion 14 while making the notched portion 86 of the pusher tube 54 face the side surface of the insertion portion 14. This makes the drainage tube 52 deform to increase the width of the notched portion 86 up to the width (the width corresponding to the diameter of the insertion portion 14) that allows the notched portion 86 to pass through the side surface of the insertion portion 14. The insertion portion 14 then extends through the notched portion 86 and enters the lumen 84. Note that it is possible to easily fit the overall pusher tube 54 on the insertion portion 14 by fitting only the distal end portion of the pusher tube 54 on the insertion portion 14 first and then gradually fitting the pusher tube 54 on the insertion portion 14 backward.

According to this arrangement, when fitting the pusher tube 54 on the outer surface of the insertion portion 14, it is not necessary to fit the pusher tube 54 on the insertion portion 14 from the distal end of the insertion portion. Even after the insertion portion 14 is inserted into the body cavity of the insertion portion 14, it is possible to fit the pusher tube 54 on the insertion portion 14 from the side surface of the insertion portion 14.

When the operator pushes the pusher tube 54 forward while holding the operation portion 82 of the pusher tube 54 after fitting the drainage tube 52 and the pusher tube 54 on the outer surface of the insertion portion 14, the distal end portion of the pusher tube 54 comes into contact with the proximal end portion of the drainage tube 52. The operator further pushes the drainage tube 52 forward while being guided by the insertion portion 14. Finally, the drainage tube 52 is pushed out forward from the distal end of the insertion portion 14.

An example of a procedure for indwelling a drainage tube in the biliary tract or the pancreatic duct by using the drainage tube insertion tool 50 will be described next. The operator fits the drainage tube 52 on the insertion portion 14 before inserting the insertion portion 14 of the endoscope 10 into the body cavity of the patient. At this time, it is preferable to indwell the drainage tube 52 on the proximal end side of the insertion portion 14. Subsequently, the operator inserts the insertion portion 14 through the mouth of the patient and then inserts the distal end of the insertion portion 14 into the biliary tract or the pancreatic duct through the opening of the papilla vater of the duodenum (in the state shown in FIG. 5). At this time, the operator may insert a guide wire 90 (see FIG. 5) into the biliary tract or the pancreatic duct, before the insertion portion 14, through the treatment tool outlet 40 by using the treatment tool insertion channel of the endoscope 10, and then may insert the insertion portion 14 into the biliary tract or the pancreatic duct while making the guide wire 90 guide the insertion portion 14.

Subsequently, the operator pushes the distal end of the insertion portion 14 to the constricted region in which the pusher tube 54 is to be indwelled, while observing, on the monitor, the observation image captured by the imaging device on the distal end portion 36 of the insertion portion 14, and holds the insertion portion 14 in this state. Note that it is not always necessary to insert the insertion portion 14 into the biliary tract or the pancreatic duct. The operator may perform the following operation while holding the distal end face 38 of the insertion portion 14 in a state in which the distal end face 38 faces the papilla vater in the duodenum, with the guide wire being inserted in the biliary tract or the pancreatic duct.

Figure 5:
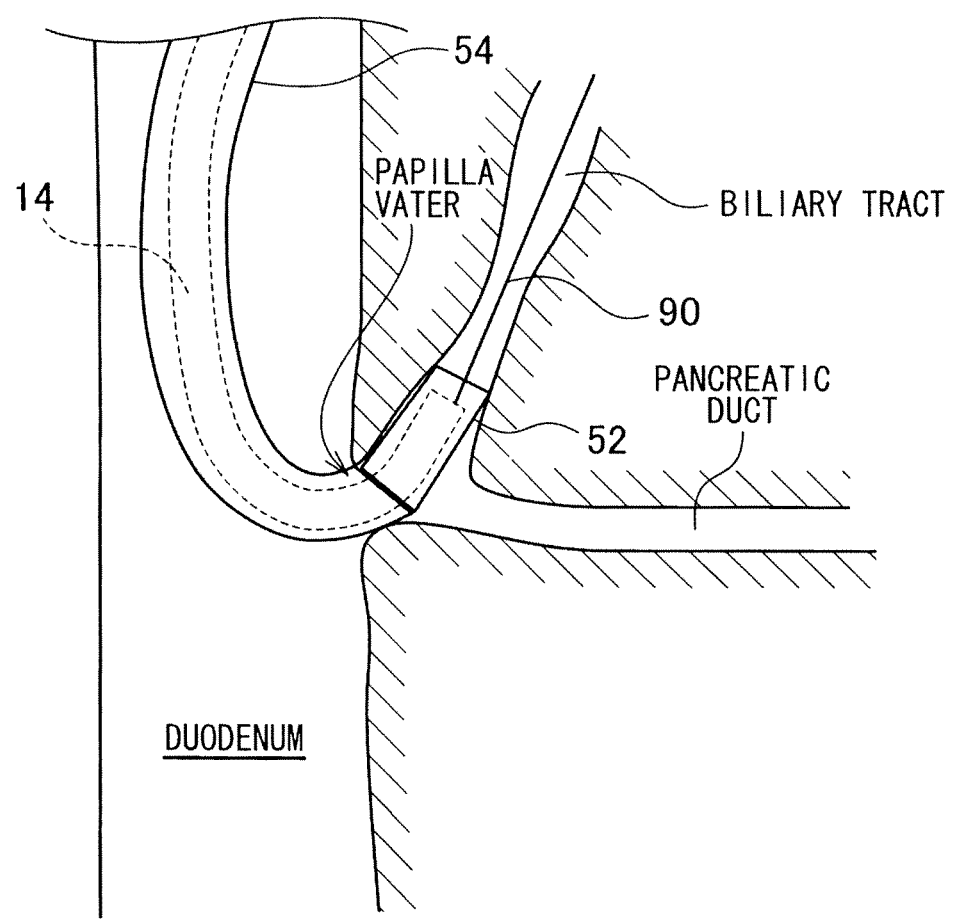
FIG. 5 is a view for explaining a procedure for the use of a drainage tube insertion tool according to the present invention.

The operator then pushes the notched portion 86 of the pusher tube 54 on the insertion portion 14 from the side surface, side of the insertion portion 14 at a position nearer to the proximal end side than the drainage tube 52 fitted on the outer surface of the insertion portion 14, and fits the pusher tube 54 on the outer surface of the insertion portion 14. The operator pushes the pusher tube 54 forward while making the insertion portion 14 guide the tube, and pushes the drainage tube 52 forward with the pusher tube 54 while making the insertion portion 14 guide the drainage tube. Thereafter, as shown in FIG. 5, the operator pushes the drainage tube 52 forward from the distal end of the insertion portion 14, and inserts the drainage tube 52 into the constricted region. With the above operation, the operator can indwell the drainage tube 52 in a desired constricted region. Note that the operator may gradually fit the pusher tube 54 on the insertion portion 14 from the distal end side to the proximal end side while pushing the pusher tube 54 to the distal end side of the insertion portion 14, with the distal end of the pusher tube 54 being fitted on the insertion portion 14 at an extra-length portion of the insertion portion 14 which is exposed outside the body cavity, instead of pushing the pusher tube 54 into the body cavity upon fitting the overall pusher tube 54 on the insertion portion 14. If the length of a portion of the insertion portion 14 which is exposed outside the body cavity is equal to or more than that of the pusher tube 54, it is possible to insert the pusher tube 54 into the body cavity upon fitting the overall pusher tube 54 on the insertion portion 14.

The embodiment described above has exemplified the drainage tube insertion tool which indwells the drainage tube in the lumen of the biliary tract or pancreatic duct. However, the present invention can also be applied to a drainage tube insertion tool which indwells the drainage tube in the lumen of a region other than the biliary tract and the pancreatic duct.

Figure 6:
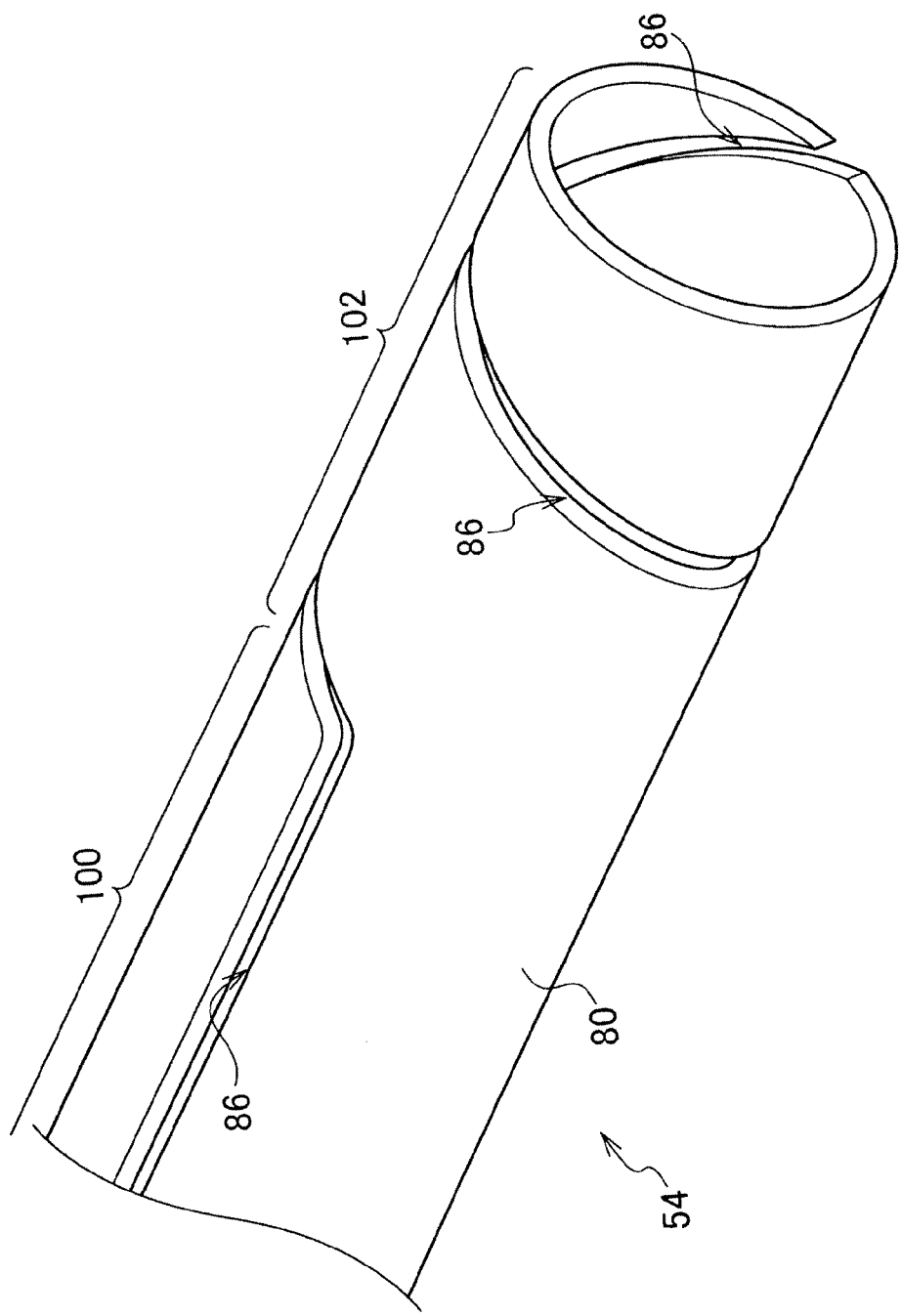
FIG. 6 is a perspective view of the distal end portion of a pusher tube showing a modification of the pusher tube.

A modification of the pusher tube 54 will be described next. According to the pusher tube 54 in the above embodiment, as shown in FIGS. 4A to 4C or the like, the notched portion 86 is linearly formed in the tube body 80 from the distal end to the proximal end along the longitudinal axis direction. As shown in FIG. 6, however, the tube body 80 may be provided with a linear notch range 100 in which the notched portion 86 (notch) is linearly formed in a side wall portion of the tube body 80 from the proximal end to a predetermined position on the distal end side of the tube body 80 as in the above embodiment in the longitudinal axis direction and a helical notch range 102 in which the notched portion 86 is helically formed in a side wall portion of the tube body 80 which is located nearer to the distal end side than the linear notch range 100. Referring to FIG. 6, the notched portion 86 in the helical notch range 102 rotates substantially one and half turns (rotates through substantially 450° around the longitudinal axis) around the side wall portion of the tube body 80. However, the number of turns the notched portion 86 rotates around the side wall portion of the tube body 80 in the helical notch range 102 is not limited to this. It is possible to set the number of turns to a desired number. It is also possible to set the number of turns to less than one.

According to this arrangement, when fitting the pusher tube 54 (tube body 80) on the outer surface of the insertion portion 14 of the endoscope 10, the operator pushes the notched portion 86 of the distal end of the helical notch range 102 to the insertion portion 14 and fits the distal end portion of the pusher tube 54 on the insertion portion 14. The operator then pushes the pusher tube 54 onto the insertion portion 14 while rotating the pusher tube 54 and gradually shifting the position of the notched portion 86 facing the insertion portion 14 toward the proximal end side of the helical notch range 102. This makes it possible to fit the helical notch range 102 of the pusher tube 54 on the insertion portion 14. After fitting the overall helical notch range 102 on the insertion portion 14, the operator pushes the notch of the linear notch range 100 to the insertion portion 14 in the same manner as in the above embodiment. This can fit the linear notch range 100 of the pusher tube 54 on the insertion portion 14. The helical notch range 102 of the pusher tube 54 which is fitted on the insertion portion 14 in this manner does not come off the insertion portion 14 only when the pusher tube 54 is pulled in one direction. This prevents the contingency that the pusher tube 54 (in particular the distal end portion) comes off the insertion portion 14 due to the bending portion of the insertion portion 14 and the like.

Figure 7:
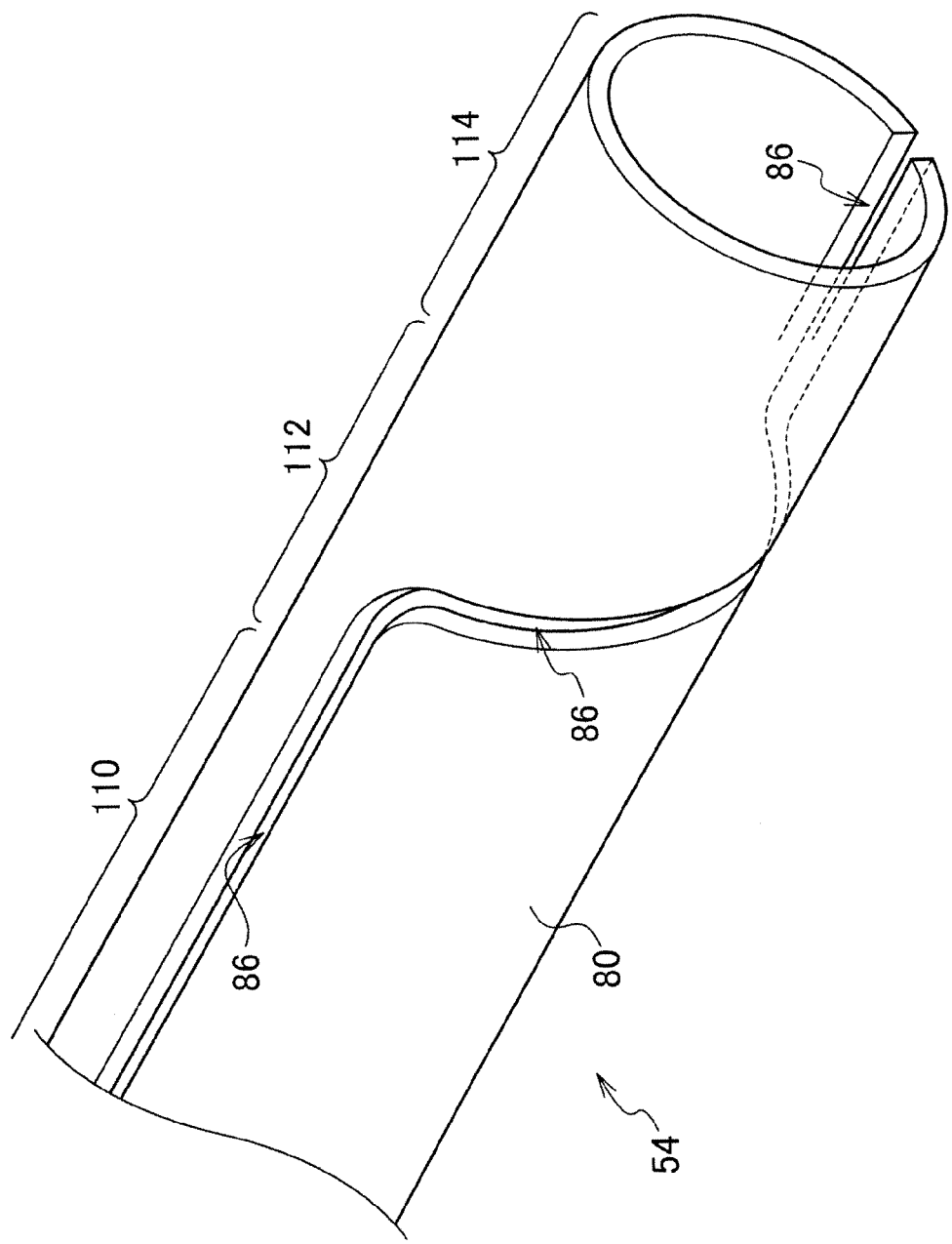
FIG. 7 is a perspective view of the distal end portion of a pusher tube showing a modification of the pusher tube.

The notched portion 86 may have the form shown in FIG. 7. In the form shown in FIG. 7, the tube body 80 is provided with a linear notch range 110 in which the notched portion 86 is linearly formed in a side wall portion of the tube body 80 in the longitudinal axis direction from the proximal end to a predetermined position on the distal end side of the tube body 80 as in the above embodiment and a helical notch range 112 in which the notched portion 86 is helically formed in a side wall portion of the tube body 80 which is located nearer to the distal end side than the linear notch range 110. In the helical notch range 112, the notched portion 86 rotates a substantially half turn (rotates through substantially 180° around the longitudinal axis) around the side wall portion of the tube body 80. The tube body 80 is also provided with a linear notch range 114 in which the notched portion 86 is linearly formed, in the longitudinal axis direction, in a side wall portion of the tube body 80 which is located nearer to the distal end side than the helical notch range 112. The notched portion 86 in the linear notch range 114 is formed at a position opposite to the position on the side wall portion in which the notched portion 86 is formed in the linear notch range 110 (at a position rotated about the longitudinal axis direction through 180°).

This arrangement can fit the helical notch range 112 of the pusher tube 54 on the insertion portion 14 in the same manner as the helical notch range 102, and can fit the linear notch ranges 110 and 114 of the pusher tube 54 on the insertion portion 14 in the same manner as the linear notch range 100. The helical notch range 112 of the pusher tube 54 fitted on the insertion portion 14 does not easily conic off the insertion portion 14. This prevents the contingency that the pusher tube 54 (in particular the distal end portion) comes off the insertion portion 14 due to the bending portion of the insertion portion 14 and the like.

Note that the present invention is not limited to the case in which the helical notch ranges 102 and 112 shown in FIGS. 6 and 7 each are provided on one specific portion, and it is possible to provide such a range on a desired portion and to provide such ranges on a plurality of portions. In addition, the number of turns of the notched portion 86 around the side wall portion of the tube body 80 in each helical notch range (the number of turns (rotational angle) around the longitudinal axis direction) can be set to an arbitrary value. As compared with the linear notch ranges 100, 110, and 114, in the helical notch ranges 102 and 112, it is not easy to insert the insertion portion 14 into the lumen 84 inside the tube body 80 from the notched portion 86. The width of the notched portion 86 in the helical notch ranges 102 and 112 is preferably larger than that of the notched portion 86 in the linear notch ranges 100, 110, and 114.

Figure 8:
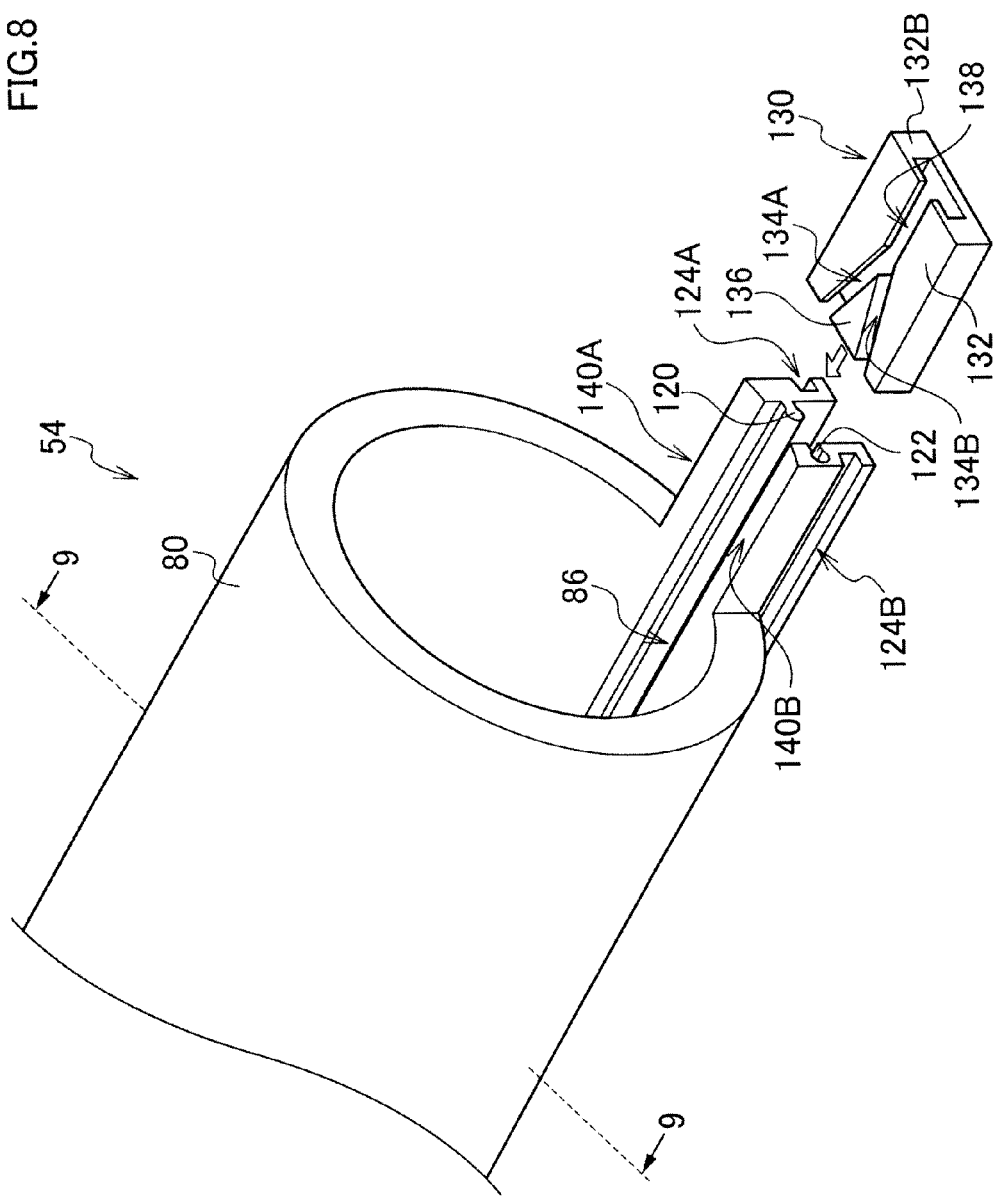
FIG. 8 is a perspective view of the distal end portion of the pusher tube showing a form in which a fastener is provided in a notched portion of the pusher tube.
Figure 9:
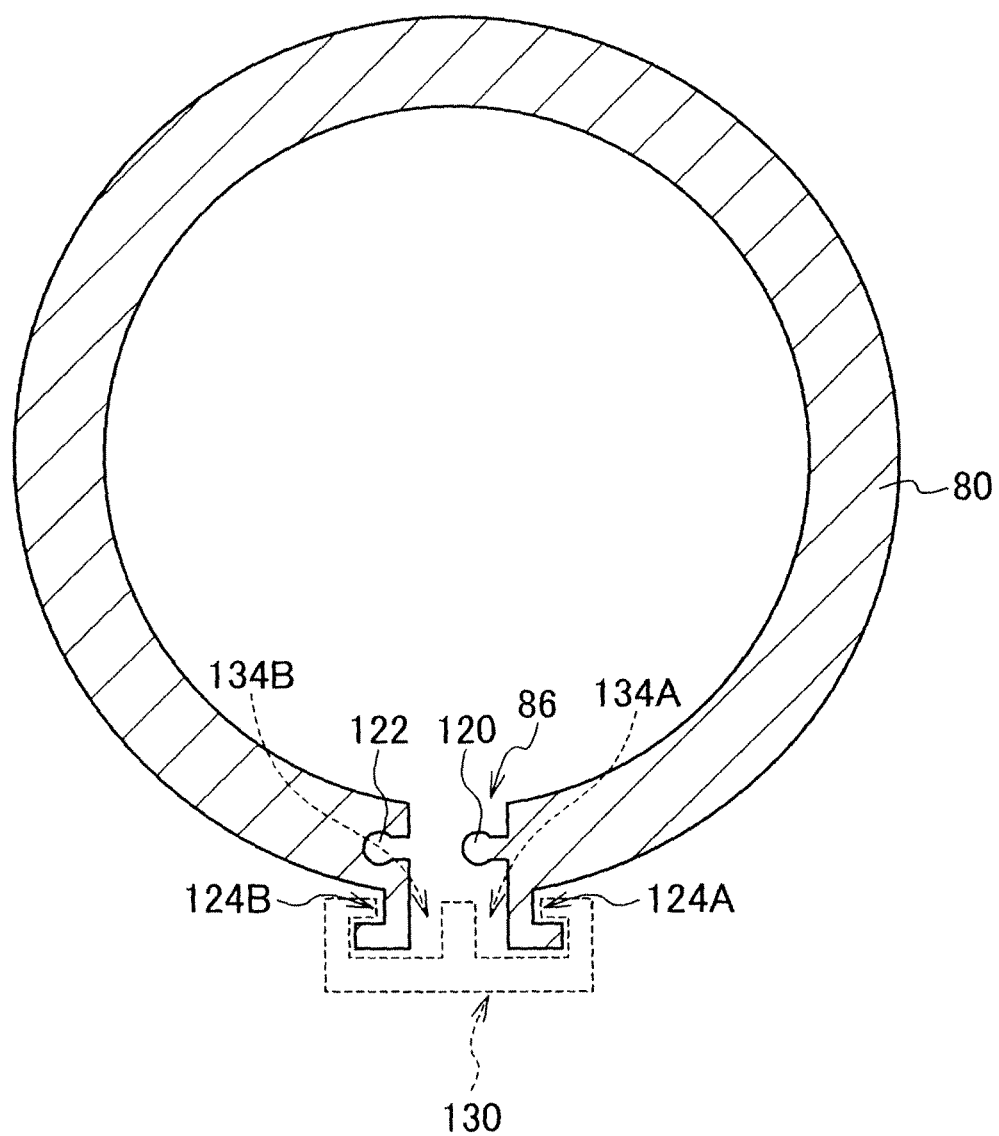
FIG. 9 is a sectional view taken along 9-9 in FIG. 8.

FIGS. 8 and 9 show a form in which a fastener (openable attachment) is provided for the notched portion 86 of the pusher tube 54. FIG. 8 is a perspective view of the distal end portion of the pusher tube 54. FIG. 9 is a sectional view (cross-sectional view) taken along 9-9 in FIG. 8. In the form shown in FIGS. 8 and 9, a convex portion 120 is formed on one of the opposing surfaces of the notched portion 86 of the tube body 80 so as to extend in the longitudinal axis direction of the pusher tube 54. A constricted portion is formed on the proximal end portion of the convex portion 120 which is smaller in width than the distal end portion. A concave portion 122 is formed in the surface facing the surface on which the convex portion 120 of the notched portion 86 is formed. The concave portion 122 has substantially the same sectional shape as the convex portion 120. The convex portion 120 and the concave portion 122 constitute a fastener on the notched portion 86. Fitting the convex portion 120 in the concave portion 122 will seal the notched portion 86.

Guide portions 124A and 124B are formed on the outer surface of the tube body 80 so as to protrude from the two sides of the notched portion 86 along the notched portion 86. A slider 130 for opening and closing the fastener constituted by the convex portion 120 and the concave portion 122 are slidably engaged with the guide portions 124A and 124B.

Figure 10:
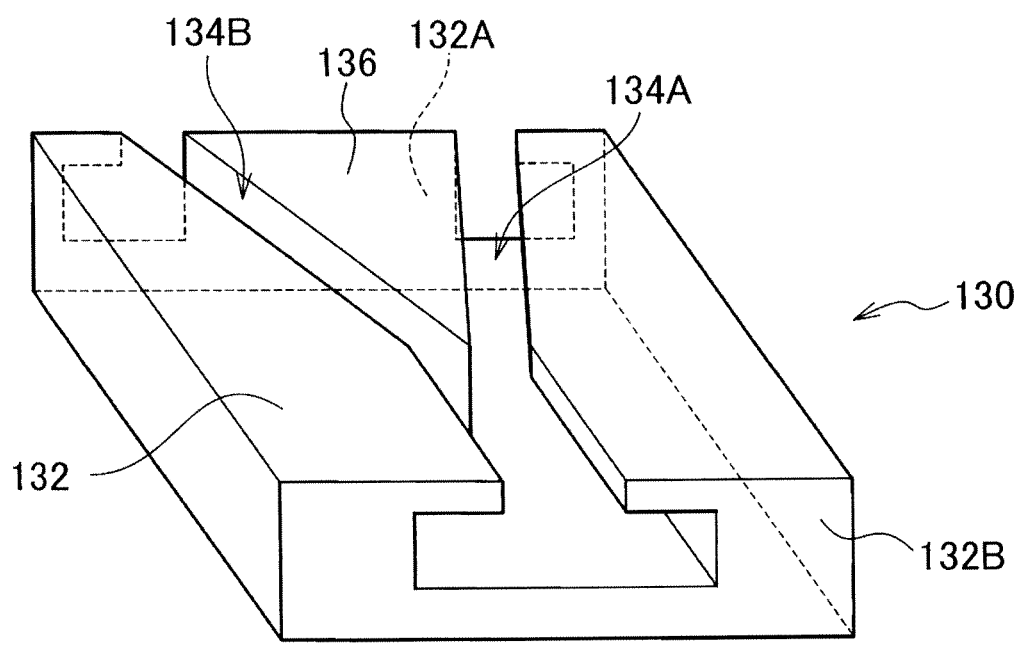
FIG. 10 is a perspective view of a slider.

The slider 130 is indicated by the solid lines in FIG. 8 and the broken lines in FIG. 9. FIG. 10 is a perspective view showing only the slider 130. FIG. 11A is a plan view of the slider 130. FIGS. 11B and 11C are respectively a sectional view taken along B-B in FIG. 11A and a sectional view taken along C-C in FIG. 11A.

As shown in these drawings, engaging grooves 134A and 134B to be respectively engaged with the guide portions 124A and 124B are formed in a substantially rectangular parallelepiped slider body 132 of the slider 130 so as to penetrate from one end face (insertion-side end face 132A) to the end face on the opposite side (exit-side end face 132B). These engaging grooves 134A and 134B are separated into two grooves by a partition column 136 on the insertion side and merge into one engaging groove 138 on the exit side. When the operator inserts, from the distal end side of the pusher tube 54, the guide portions 124A and 124B into the engaging grooves 134A and 134B from the insertion-side end face 132A of the slider 130, and slides the slider 130 to the proximal end side of the pusher tube 54, the convex portion 120 of the notched portion 86 engages with the concave portion 122 so as to make sealing in the engaging groove 138 on the exit side. In this state, the convex portion 120 and the concave portion 122 protrude from the exit-side end face 132B of the slider 130.

As shown in FIG. 8, leading portions 140A and 140B respectively constituted by the convex and concave portions 120 and 122 and guide portions 124A and 124B of the notched portion 86 may be formed on the distal end portion of the pusher tube 54 so as to extend in the longitudinal axis direction. This structure allows to easily insert the leading portions 140A and 140B into the engaging grooves 134A and 134B of the slider 130, respectively. However, it is not always necessary to provide the leading portions 140A and 140B.

According to the form in which the fastener provided for the notched portion 86 of the pusher tube 54 in the above manner, when fitting the pusher tube 54 (tube body 80) on the outer surface of the insertion portion 14 of the endoscope 10, the operator pushes the notched portion 86 onto the insertion portion 14 while the fastener of the notched portion 86 is open, and fits at least the distal end side of the pusher tube 54 on the insertion portion 14. The operator then inserts the guide portions 124A and 124B on the distal end of the pusher tube 54 into the engaging grooves 134A and 134B, respectively, from the insertion-side end face 132A side of the slider 130, and slides the slider 130 toward the proximal end side along the guide portions 124A and 124B. This seals the portion of the notched portion 86 which is fitted on the insertion portion 14 of the pusher tube 54. Sliding the slider 130 to the proximal end of the pusher tube 54 upon fitting the pusher tube 54 on the insertion portion 14 up to the proximal end side will seal the overall notched portion 86 of the pusher tube 54. In this manner, the notched portion 86 of the pusher tube 54 fitted on the insertion portion 14 is sealed by the fastener. This prevents the contingency that the pusher tube 54 comes off the insertion portion 14 due to the bending portion of the insertion portion 14 and the like.

Note that instead of the slider 130 described above, a slider portion 154 having a structure similar to that of the slider 130 may be formed in a passage hole 152 of a mouthpiece 150 of the endoscope, as shown in FIGS. 12A and 12B. FIG. 12A is a longitudinal sectional view of the mouthpiece 150. FIG. 12B is a front view of the mouthpiece 150. The same reference numerals of the constituent elements of the slider 130 denote the same constituent elements of the slider portion 154 in FIGS. 12A and 12B, and a description of them will be omitted.

According to this structure, when fitting the pusher tube 54 on the insertion portion 14 of the endoscope 10 and pushing the pusher tube 54 into the body cavity of a patient along the insertion portion 14 after inserting the insertion portion 14 into the body cavity through the passage hole 152 of the mouthpiece 150, the operator can insert the pusher tube 54 into the body cavity while the notched portion 86 of the pusher tube 54 is sealed, by engaging the guide portions 124A and 124B of the pusher tube 54 with the engaging grooves 134A and 134B of the slider portion 154 of the mouthpiece 150, respectively, and making the guide portions 124A and 124B pass through the engaging grooves 134A and 134B.

What is claimed is:

1. An endoscope assembly, comprising:
   an endoscope;
   a drainage tube configured to slidably fit on an outer surface of an insertion portion of the endoscope; and
   a pusher tube configured to slidably fit on the outer surface of the insertion portion of the endoscope and which pushes the drainage tube,
   wherein a notch is formed in a side wall portion of the pusher tube along a longitudinal axis direction,
   wherein the pusher tube is fitted on the outer surface of the insertion portion upon making the insertion portion intrude from outside of the pusher tube to inside of the pusher tube through the notch, and the drainage tube is inserted into a predetermined lumen of a body cavity by pushing the drainage tube to protrude beyond a distal end of the insertion portion with the pusher tube, and
   wherein the notch extends from a distal end of the pusher tube to a proximal end of the pusher tube.

2. The endoscope assembly according to claim 1, wherein a width of the notch in a direction perpendicular to the longitudinal axis direction is smaller than a diameter of the insertion portion.

3. The endoscope assembly according to claim 1, wherein the drainage tube has flexibility.

4. The endoscope assembly according to claim 2, wherein the drainage tube has flexibility.

5. The endoscope assembly according to claim 1, wherein an operation portion is formed on a proximal end portion of the pusher tube so as to protrude toward the outer surface.

6. The endoscope assembly according to claim 2, wherein an operation portion is formed on a proximal end portion of the pusher tube so as to protrude toward the outer surface.

7. The endoscope assembly according to claim 3, wherein an operation portion is formed on a proximal end portion of the pusher tube so as to protrude toward the outer surface.

8. The endoscope assembly according to claim 4, wherein an operation portion is formed on a proximal end portion of the pusher tube so as to protrude toward the outer surface.

9. The endoscope assembly according to claim 1, wherein the notch is helically formed in a predetermined range of the pusher tube in a longitudinal axis direction.

10. The endoscope assembly according to claim 1, wherein a fastener is formed in the notch, and the notch is configured to be opened and closed by the fastener.

11. The endoscope assembly according to claim 1, wherein the notch is formed such that an interior of the pusher tube is exposed.

12. The endoscope assembly according to claim 1, wherein the drainage tube is guided along the outer surface of the insertion portion while being pushed by the pusher tube.

13. The endoscope assembly according to claim 1, wherein the drainage tube includes stop portions which are formed on the outer surface of the drainage tube on a distal end side and a proximal end side of the drainage tube so as to obliquely protrude toward a middle portion of the drainage tube.

14. The endoscope assembly according to claim 1, wherein the drainage tube is supported on the insertion portion so as to be slidable in the longitudinal axis direction.

15. The endoscope assembly according to claim 1, wherein the pusher tube has a C-shaped cross-section.

16. The endoscope assembly according to claim 1, wherein an operation portion is formed on a proximal end portion of the pusher tube so as to protrude toward the outer surface, and wherein a width of the notch increases towards the proximal end portion of the pusher tube.

17. The endoscope assembly according to claim 1, wherein the notch is linearly formed along the longitudinal axis direction so as to expose an interior of the pusher tube.

* * * * *